(12) United States Patent
Desgorces (10) Patent No.: US 9,691,252 B2
(45) Date of Patent: Jun. 27, 2017

(54) FLOOR COVERING ITEM FOR DETECTING DROPPAGES

(71) Applicant: ABCD INNOVATION, Paris (FR)

(72) Inventor: Claude Desgorces, Gujan Mestras (FR)

(73) Assignee: ABCD INNOVATION, Paris (FR)

( * ) Notice: Subject to any disclaimer, the term of this patent is extended or adjusted under 35 U.S.C. 154(b) by 251 days.

(21) Appl. No.: 14/394,562

(22) PCT Filed: Apr. 8, 2013

(86) PCT No.: PCT/FR2013/050760
§ 371 (c)(1),
(2) Date: Oct. 15, 2014

(87) PCT Pub. No.: WO2013/156707
PCT Pub. Date: Oct. 24, 2013

(65) Prior Publication Data
US 2015/0054649 A1    Feb. 26, 2015

(30) Foreign Application Priority Data

Apr. 19, 2012  (FR) ..................................... 12 01156
Mar. 8, 2013   (FR) ..................................... 13 52109

(51) Int. Cl.
G08B 23/00      (2006.01)
G08B 21/04      (2006.01)
(Continued)

(52) U.S. Cl.
CPC ........ *G08B 21/0446* (2013.01); *A61B 5/1117* (2013.01); *A61B 5/6889* (2013.01);
(Continued)

(58) Field of Classification Search
CPC .............. G08B 21/0446; G08B 21/043; G08B 21/0469; G08B 13/10; A61B 5/1117;
(Continued)

(56) References Cited

U.S. PATENT DOCUMENTS 4,888,581 A  * 12/1989  Guscott .............. G08B 21/0469
                                                    200/61.93
9,316,549 B2 *  4/2016  Wu .......................... G01L 1/205
(Continued)

FOREIGN PATENT DOCUMENTS

EP    2 050 426 A1    4/2009
FR    1 102 512 A    10/1955
WO    01/08755 A1    2/2001

OTHER PUBLICATIONS

International Search Report, dated Jun. 19, 2013, from corresponding PCT application.

*Primary Examiner* — Hai Phan
*Assistant Examiner* — Royit Yu
(74) *Attorney, Agent, or Firm* — Troutman Sanders LLP (57) ABSTRACT

A covering component for detecting falls includes: a body delimited by edges, a plurality of pressure sensors distributed in accordance with a selected geometry in the body, a processing unit connected to at least some of the pressure sensors and which is arranged to collect state information of these pressure sensors, and at least a first socket and a second socket, each of which is connected to the processing unit which is arranged in the region of an edge, and which is arranged so as to be able to be connected to a socket of another similar component. The processing unit is arranged to: associate location information taken from this state information with location information of the component, receive via the first socket information originating from a first other similar component, and transmit, via the second socket, the associated information and/or received information to a second other similar component.

12 Claims, 5 Drawing Sheets

(51) Int. Cl.
*A61B 5/00* (2006.01)
*A61B 5/11* (2006.01)
*G08B 13/10* (2006.01)

(52) U.S. Cl.
CPC ....... *G08B 21/043* (2013.01); *G08B 21/0469* (2013.01); *A61B 2562/0247* (2013.01); *A61B 2562/046* (2013.01); *G08B 13/10* (2013.01)

(58) Field of Classification Search
CPC .. A61B 2562/046; G04G 19/21; G04G 13/02; G04G 21/02; G06F 1/14; G06F 1/3206
USPC ...................................................... 340/573.1
See application file for complete search history.

(56) References Cited

U.S. PATENT DOCUMENTS

| | | | | |
|---|---|---|---|---|
| 2006/0049942 A1* | 3/2006 | Sakama | ............. | G06K 7/10178 340/572.1 |
| 2006/0171570 A1* | 8/2006 | Brendley | ............... | G08B 13/10 382/115 |
| 2009/0221332 A1* | 9/2009 | Bamberger | .......... | H04B 1/3805 455/572 |
| 2010/0297597 A1* | 11/2010 | Kim | ........................ | G09B 5/06 434/362 |
| 2011/0004435 A1* | 1/2011 | Lindstrom | ......... | G08B 21/0469 702/138 |
| 2011/0279276 A1* | 11/2011 | Newham | ............... | A61B 5/1115 340/573.4 |
| 2012/0051260 A1* | 3/2012 | Tamaki | ................. | H04W 24/02 370/253 |
| 2012/0309531 A1* | 12/2012 | Gong | ................... | H03K 17/955 463/36 |

* cited by examiner

FLOOR COVERING ITEM FOR DETECTING DROPPAGES

FIELD OF THE INVENTION

The invention relates to the field of floor covering components, and more specifically floor coverings which are capable of detecting the fall of a person.

All developed countries are experiencing an increased ageing of their populations. This ageing can be seen in a very sharp increase of the number of people aged 60 and over. This situation creates a real challenge in the field of public health. It also creates serious problems in the management of the dependency of elderly people.

BACKGROUND

This is because elderly people are seeing their life expectancy increase every year. Furthermore, the evolution of social structures results in these people leading a more and more solitary existence, or living within specialised structures.

For people living alone, this isolation is an acute problem since they are at risk of dying of the consequences of a fall owing to an inability to call for assistance. In the case of specialised structures, the detection of falls is also very important if it is desirable to keep care staff at a reasonable level and a realistic cost for providing care, without for all that risking cases of litigation regarding responsibility for lack of supervision.

The increasing awareness of these problems has resulted in studies being carried out which have shown that more than 7500 people die each year in France as a result of a fall which has not been detected in time, or from the consequences of a fall which has not been dealt with in a timely manner.

The Applicant has proposed a device which allows such falls to be detected and which is, for example, in the form of a carpet or complete floor with standard dimensions. This device is described in the French patent application FR 11/02512. Such a device can be used in a hospital or in a retirement home, for example, and is based on the conversion of pressure brought about by a fall into an electrical signal which is associated with a known location in order to detect this fall. These devices may include all the floors of a health establishment, or at least the portions thereof which are intended to be walked on by elderly persons.

Such devices are appreciated and comply with their objectives. However, their creation has led to the occurrence of another requirement. The Applicant has found that the design and the production of such devices are carried out without taking into account the specific nature of the locations in which they are intended to be installed. This limits the suitability of "sensitive carpets" for their intended environment, that is to say, bedrooms, corridors and communal rooms. This is because the diversity of shapes and surfaces of floors to be covered is great. Consequently, either there is proposed a range of very varied shapes and surfaces of carpet and coverings, even made-to-measure, at high costs, or there is proposed a restricted range of models which are less adaptable but at a limited cost. This is not entirely satisfactory.

On the other hand, these sensitive floor coverings involve the use of electrical cabling in a quantity which is substantially proportional to the covering surface. When significant surfaces have to be covered, such as corridors of health establishments, the electrical cabling becomes a critical parameter as a result of the spatial requirement thereof and the quantity thereof. The increase of costs associated with the electrical cabling makes all the more worthwhile the efforts which are intended to limit the use thereof, both from the point of view of the quantity of cables required, and from the point of view of the time required to assemble it.

SUMMARY

The invention is intended to improve the situation.

To this end, the invention proposes a covering component for detecting falls comprising:
  a body which is delimited by edges,
  a plurality of pressure sensors which are distributed in accordance with a selected geometry in the body,
  a processing unit which is connected to at least some of the pressure sensors and which is arranged to collect status information of these pressure sensors, and
  at least a first socket and a second socket, each of which is connected to the processing unit which is arranged in the region of an edge, and arranged so as to be connectable to a socket of another similar component.

The processing unit is arranged so as to
  associate location information which is derived from the status information with location information of the component,
  receive, via the first socket, information originating from a first other similar component, and
  transmit, via the second socket, the associated information and/or the received information to a second other similar component.

Furthermore, such a component may have the following optional features:
  the surface layer and the lower layer each comprise a film which carries, on opposing faces, a set of conductive strips, the conductive strips being substantially parallel within each set, and the sets of conductive strips being arranged so that the conductive strips of separate sets are substantially perpendicular to each other and cross each other region of the recesses of the intermediate layer, in order to form a pressure sensor each time,
  the body is generally rectangular or square, the processing unit being arranged in a corner of the body.

According to another aspect, the invention relates to a kit which comprises a set of several components. The kit may further comprise a central unit for the detection of a fall, including:
  a socket which is capable of being connected to at least one socket of at least one component,
  a processor which is connected to the socket and which is arranged so as to
  collect from pressure sensors status information which is associated with location information of the pressure sensors which is linked to component identification information,
  calculate from the information collected a status matrix of an assembly of interconnected components,
  detect an alert status from the status matrix,
  transmit an alert signal which is selected in accordance with the alert status detected.

BRIEF DESCRIPTION OF THE DRAWINGS

Other features and advantages of the invention will be better appreciated from a reading of the following description, taken from examples which are given by way of non-limiting illustration and taken from the drawings, in which.

DETAILED DESCRIPTION

The following drawings and description contain, for the most part, elements of a specific nature. They can therefore not only serve to provide better understanding of the present invention, but also contribute to the definition thereof, where applicable.

Figure 1:
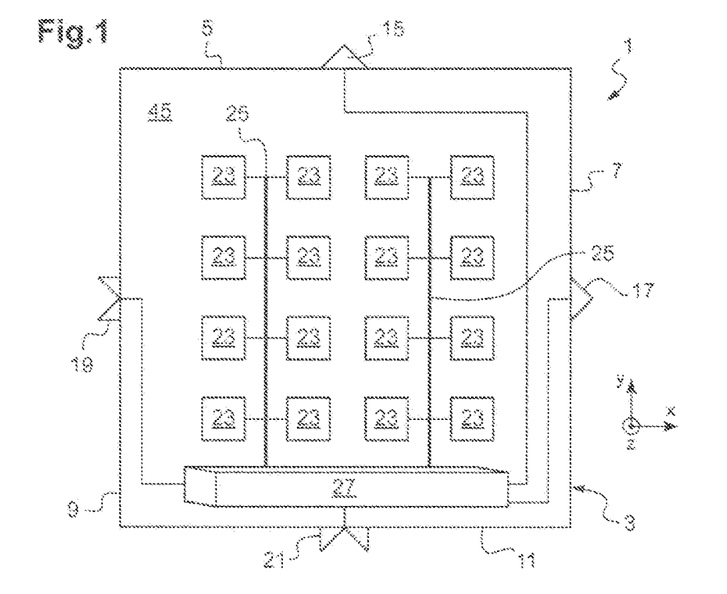
FIG. 1 is a schematic top view of a coating component according to the invention, in which a surface layer of the component has been removed.

As can be seen in FIG. 1, a covering component 1 comprises a body 3 which is delimited by edges 5, 7, 9, 11, sockets 15, 17, 19, 21, pressure sensors 23, cables 25 and a processing unit 27.

The term "component" is used here in the general sense thereof, and refers to an element which is intended to be an integral portion of a wider assembly, of an assembly, in the manner of a piece of a puzzle. The term "component" is intended in particular to refer to a floor covering element, such as a tile, a slab, a strip or any other type.

The component 1 comprises a surface layer of the body 3 which is not illustrated in FIG. 1 in order to allow the "inner side" of the covering component 1 to be seen. In the example described herein, the body 3 is of flattened shape and has two main directions and a thickness direction which are illustrated by the reference (x; y; z). The body 3 is substantially of square shape defined by the four edges 5, 7, 9 and 11. In order to facilitate the description, the edge 5 will be referred to below as the "north edge", the edge 7 as the "east edge", the edge 9 as the "west edge" and the edge 11 as the "south edge". This designation is independent of the actual orientation of the covering component 1 once installed. The edges 5, 7, 9 and 11 each support one of the sockets 15, 17, 19 and 21, respectively. The body 3 is approximately 60 cm long per side in example here described. In a variant, the body 3 may measure between 20 cm and 150 cm per side, for example, 100 cm, that is to say, a surface-area between 400 $cm^2$ and 2.25 $m^2$.

In other variants, the body 3 may have a shape other than square, for example, rectangular or any other polygon or shape having a suitable closed contour. The covering component 1 being intended to be assembled with other similar covering components, the shape and the dimensions of the body 3 are selected to have corresponding shapes. That is to say, the body 3 forms a mesh having a pattern which comprises a plurality of assembled covering components. The shapes and dimensions of the body 3 of the covering components 1 may be adapted to correspond to aesthetic or functional criteria whilst still remaining able to be combined with each other, in the manner of other elemental conventional floor covering components, such as parquet panels or tiling.

As will be seen below, the body 3 has an upper or surface layer 41 and a lower or base layer 45.

The lower layer 45 of the body 3 supports the processing unit 27 and the pressure sensors 23. The processing unit 27 will be described in greater detail with reference to FIG. 3.

Each sensor 23 is in this instance electrically connected to the processing unit 27. This electrical connection is provided by conductive wires 25. In the example described in this instance, the processing unit 27 comprises sixteen inputs, each one of which is connected to a conductive wire 25 which is itself connected to one of the pressure sensors 23. The processing unit 27 comprises in this instance at least as many inputs as pressure sensors 23 which are associated therewith, to which there are added four inputs/outputs which are connected to the sockets 15, 17, 19 and 21. In a variant, the connections between the pressure sensors 23 and the processing unit 27 are produced using one or more flat flexible cables or sheets, for example, sold by the company Axon under the name "Axojump (registered trade mark)— Flat flexible cables". The processing unit 27 is on the other hand connected to each of the sockets 15, 17, 19 and 21. These electrical connections are provided in this instance by electrical cables which resemble those which connect the pressure sensors 23 to the processing unit 27. Any other suitable electrical connection means may be envisaged by the person skilled in the art.

Figure 2:
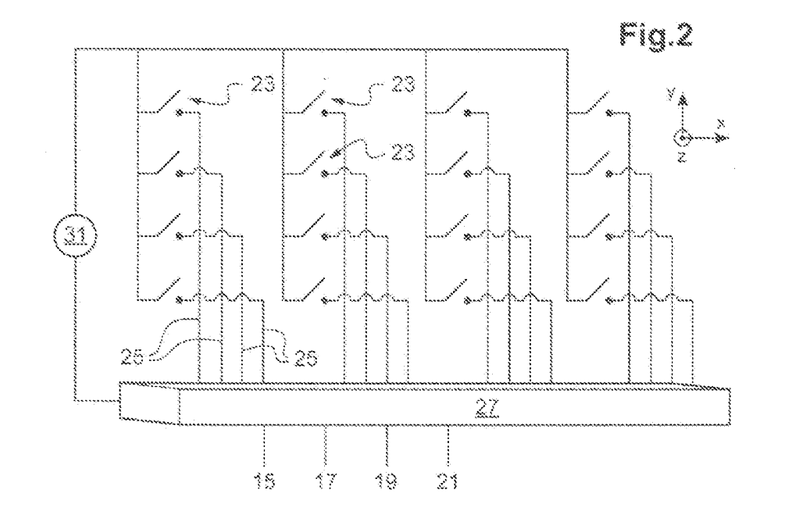
FIG. 2 is a simplified electrical diagram of a detection portion of the component of FIG. 1.

FIG. 2 is a simplified electrical diagram of a detection portion of the component 1 comprising the pressure sensors 23 and the processing unit 27. When no pressure is detected, the pressure sensors 23 are in this instance equivalent to switches in the open position. When a pressure is detected, they are equivalent to switches in the closed position. The covering component 1 comprises an electrical source 31. With the exception of FIG. 2 and for reasons of clarity, the electrical sources are not illustrated in the Figures. At least one of the sockets 15, 17, 19 and 21 includes in this instance an electrical source 31. When a pressure sensor 23 is subjected to a pressure, the electrical loop is closed. The processing unit 27 is capable of determining the status of each of the pressure sensors 23 by means of interpretation of current variations.

The pressure sensors 23 are distributed over the surface of the lower layer 45 in accordance with a selected geometry. In the example described here, there are sixteen pressure sensors 23 which are organised in a regular manner in four lines in the direction x and four columns in the direction y, thus defining a sensor matrix. The individual structure and operation of an embodiment of the pressure sensors 23 will be described with reference to FIGS. 6 to 8. Another embodiment will be described with reference to FIG. 13.

Figure 3:
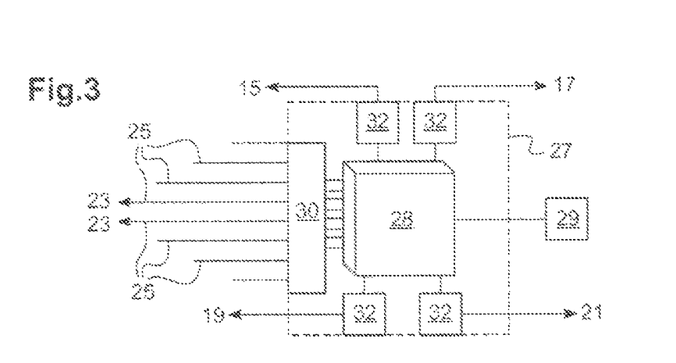
FIG. 3 is a simplified electrical diagram of an element of FIG. 2 and the environment thereof.

FIG. 3 shows the processing unit 27 of FIG. 2 and the environment thereof. The processing unit 27 comprises in this instance a microcontroller 28 which is known under the reference "PIC24FJ64GA306". The above-mentioned reference is adapted for a matrix of ten lines and ten columns, that is, one hundred sensors 23. The microcontroller 28 is selected in particular so that the properties thereof comply with the matrix of sensors 23 to be connected. The processing unit 27 is connected to a mass storage 29. The microcontroller 28 is connected to a "sensor" port 30 and to four "socket" ports 32. The "sensor" port 30 is arranged so as to be connected to the pressure sensors 23 via the wires 25. The four "socket" ports are each arranged so as to be connected to one of the sockets 15, 17, 19 and 21. The processing unit 27 comprises in this instance, at least as many inputs as pressure sensors 23 which are associated therewith (that is, sixteen in this instance), to which there are added four inputs/outputs which are connected to the sockets 15, 17, 19 and 21. As will be seen below, it is during an operation for configuration of the component 1 that each input/output will be defined as an input or an output, in accordance with the situation. The operation of the processing unit 27 will be described in greater detail with reference to FIGS. 9 to 12.

Figure 4:
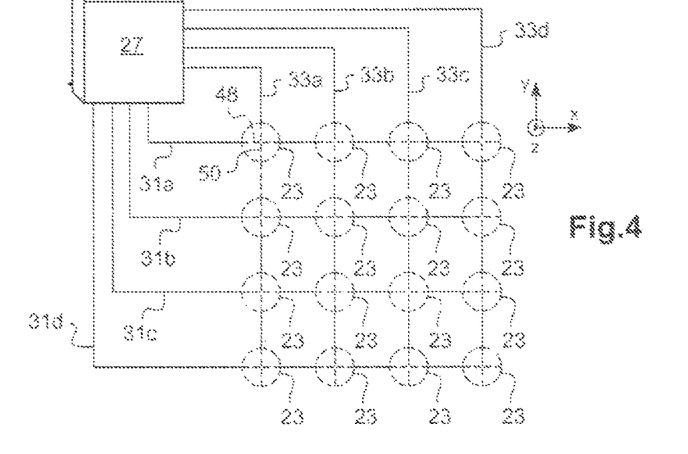
FIG. 4 is a simplified electrical diagram of a detection portion of the component of FIG. 1 according to another embodiment.

FIG. 4 shows another embodiment of the detection portion of the component 1. The pressure sensors 23 are, here also organised in four lines in the direction x and four columns in the direction y. Each sensor 23 comprises in this instance an upper portion 48 which is supported by the surface layer and a lower portion 50 which is supported by the lower layer 45. The surface layer 41 and the lower layer 45 are not illustrated. The upper portions 48 of the pressure sensors 23 of each of the lines are connected to the processing unit 27 by a common conductor wire 31a, 31b, 31c, 31d. In a similar manner, the lower portions 50 of the pressure sensors 23 of each of the columns are connected to the processing unit 27 by a common conductor wire 33a, 33b, 33c, 33d. The processing unit 27 may, for example, be the one described below with reference to FIG. 5. In the example described in this instance, the upper portions 48 are portions of one of the conductive wires 31a, 31b, 31c, 31d. In the same manner, the lower portions 50 are portions of one of the common conductor wires 33a, 33b, 33c, 33d. In the example described in this instance, the wires of the lines are arranged in the main direction x of the body 3 whilst the wires of the columns are arranged perpendicularly relative to the first ones and in the main direction y.

When a pressure which has a component in the direction of the thickness z of the component 1 is applied in the region of a pressure sensor 23, the upper portion 48 and the lower portion 50 are brought into contact. That is to say, an electrical contact is established between the wire of the line 31a, 31b, 31c, 31d concerned and the wire 33a, 33b, 33c, 33d of the column concerned, in the manner of a switch which closes. In this configuration, each crossing of the line wires 31a, 31b, 31c, 31d and column wire 33a, 33b, 33c, 33d defines a pressure sensor 23.

In a variant, the conductor wires may be adapted in the region of the crossings, and therefore the pressure sensors 23, so as to have more extensive electrical contact surfaces than a crossing of two wires. For example, the portions of wires concerned may be provided with contactors or substantially planar surfaces which are orientated facing the opposite conductor wire. In another variant, the conductor wires may be replaced by flexible strips which comprise a conductive material. Conductive materials which it is possible to use include, for example, copper or aluminium. The contact surface of a strip enables better reproducibility and reduces the risk of non-detection with respect to the wires. The pressure sensors 23 may be a combination of wires and conductive strips. The embodiment illustrated in FIG. 13 comprises an assembly of conductive strips which will be described below.

During operation, the processing unit 27 successively supplies each of the lines (or columns) with electrical power whilst reading/detecting the variations of current in each of the columns (or lines). Such a successive reading of the lines (or columns) allows the processing unit 27 to determine which intersections of each of the conductive wires are in electrical contact and therefore the individual state of each of the pressure sensors 23. The number of conductive wires between the pressure sensors 23 and the processing unit 27 and the number of inputs of the processing unit 27 dedicated to the pressure sensors 23 are thus reduced (eight instead of sixteen) in the example described herein. The number of wires and inputs of the detection portion for the processing unit 27 is equal to the sum of the lines and columns of the sensor matrix, in this instance 4+4. The signals originating from the pressure sensors 23 are multiplexed.

Figure 5:
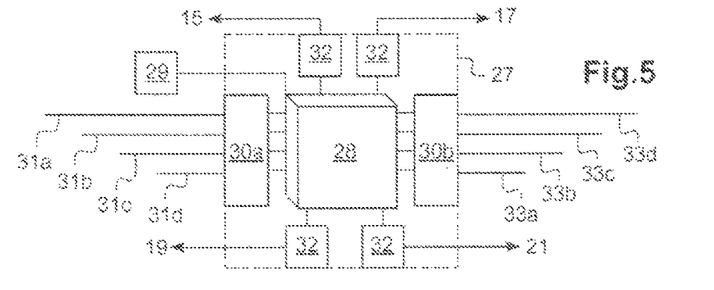
FIG. 5 is a simplified electrical diagram of an element of FIG. 4 and the environment thereof.

FIG. 5 shows the processing unit 27 of FIG. 4 and the environment thereof. The processing unit 27 comprises in this instance a microcontroller 28 known under the reference "PIC24FJ64GA306". The processing unit 27 is connected to a mass storage 29. The microcontroller 28 is connected to a "sensor/line" port 30a, to a "sensor/column" port 30b and to four "socket" ports 32. The "sensor/line" port 30a and "sensor/column" port 30b are arranged so as to be connected to the pressure sensors 23 by means of wires 31a, 31b, 31c, and 31d, or 33a, 33b, 33c and 33d, respectively, which will be described in greater detail below. The four "socket" ports are each arranged so as to be connected to one of the sockets 15, 17, 19 and 21. The processing unit 27 comprises in this instance fewer inputs (eight) than the processing unit described with reference to FIG. 3. Four inputs/outputs which are connected to the sockets 15, 17, 19 and 21 supplement these eight inputs. As will be seen below, it is during an operation for configuration of the component 1 that each input/output will be defined as an input or as an output, in accordance with the situation. The operation of the processing unit 27 will be described in greater detail with reference to FIGS. 9 to 12.

Figure 6:
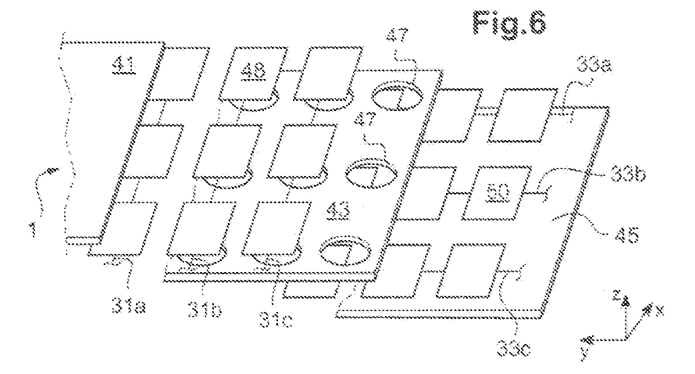
FIG. 6 is an exploded view of a portion of the component of FIG. 1.

As can be seen in FIG. 6, the body 3 of the covering component 1 comprises the surface layer 41, an intermediate layer 43 and the lower layer 45. The arrangement of the component 1 in this instance is a variant of the embodiment of FIG. 4 which allows multiplexing. The upper portion 48 and the lower portion 50 of each pressure sensor 23 comprise a plate of conductive material. These plates are connected:

via lines for the upper portions 48 via conductive wires 31a, 31b and 31c, and
via columns for the lower portions 50 via conductive wires 33a, 33b and 33c.

The intermediate layer 43 is located below the surface layer 41, in contact with the upper portions 48 and, on the lower layer 45, in contact with the lower portions 50. In the example described in this instance, the intermediate layer 43 is produced from an electrically insulating material, for example, a layer of insulating plastics material. In this instance, perforated polyester is used. In a variant, a film based on polypropylene (PP), for example, for the fire-resistant properties thereof, or polyimide is used. The surface layer 41 and/or the lower layer 45 may also be produced from a film of polyester, polypropylene (PP) or polyimide. According to the embodiments, the surface layer 41, the intermediate layer 43 and the lower layer 45 may be produced from the same material or from separate materials.

The intermediate layer 43 comprises a multiplicity of recesses 47 or holes which leave the upper portions 48 facing the lower portions 50.

The recesses 47 are through-holes in the direction of the thickness z, which are formed in a regular manner in the intermediate layer 43. In the example described here, these recesses 47 have a circular form which has a radius of 1 cm. In other embodiments, the shape of these recesses 47 may vary and may, for example, be a rectangle, a lozenge, or any other suitable polygon, or any closed contour, in particular formed by means of revolution. The recess 47 has a surface which is selected, for example, to be between 1 cm$^2$ and 9 cm$^2$, for a thickness of the intermediate layer 43 of between approximately 75 μm and 12 mm, for example, 100, 200 or 300 μm. In the example described here, the recesses 47 are circular having a diameter of approximately 10 mm, or a surface of approximately 0.8 cm$^2$ for a thickness of the intermediate layer 43 of approximately 100 μm.

Consequently, the recesses 47 are provided in order to allow the deformation of the surface layer 41 through them, so that the upper portions 48 come close to and/or into contact with (adjoin) the lower layer 45.

In the example described herein, the surface layer 41 is superimposed on the intermediate layer 43 which is itself superimposed on the lower layer 45, in this order. That is to say, the intermediate layer 43 is sandwiched between the surface layer 41 at the top and the lower layer 45 at the bottom.

Figure 7:
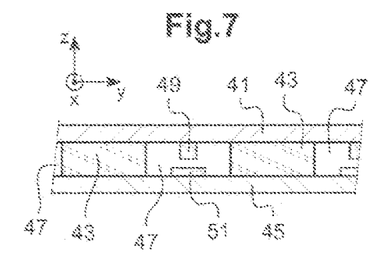
FIG. 7 is a partially sectioned view of a covering component at rest of FIG. 6.
Figure 8:
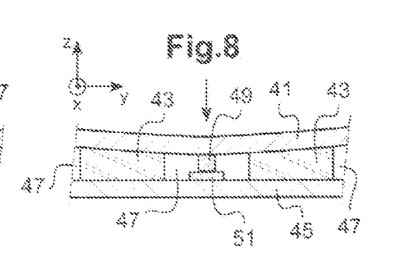
FIG. 8 is a partial sectioned view similar to FIG. 7 when the component is subjected to pressure.

FIGS. 7 and 8 are sectioned views of a covering component 1 in the rest state and in response to a pressure which has a vertical component, respectively. The arrangement of the component 1 is, in this instance, a variant in accordance with the embodiment of FIG. 2 in which each pressure sensor operates in the manner of a switch of a loop which is separate from that of the other sensors 23.

The surface layer 41 comprises an electrical conductor 49 which extends in several parallel lines in the direction x of the covering component 1.

In the example described in this instance, the conductor 49 is a single electrical wire which has a diameter of approximately 1 mm, which is connected to an electrical power supply which is not illustrated. The conductor wire 49 rests in the example described here on a lower face of the surface layer 41 which electrically insulates it. The conductor wire 49 may or may not be further insulated by a sheath. The diameter of this electrical wire 49 may vary in accordance with the needs in terms of current and power supply options envisaged. This single electrical wire 49 may be replaced by a plurality of wires which are electrically insulated from each other and which are each connected to an independent electrical power supply. This may also be a conductor system for example, of the mono or multi-conductor printed circuit type, or the like. This may also be a conductive layer which covers the lower face of the surface layer 41.

The conductive wire 49 has the function of deforming under pressure in a substantially vertical direction z in order to establish electrical contact which allows this pressure to be detected.

The intermediate layer 43 is similar to that described with reference to FIG. 6. The recesses 47 are, in this instance, provided to allow the deformation of the surface layer 41 through them so that the conductor wire 49 moves close to and/or into contact with or adjoins the lower layer 45. The portion of the conductor wire 49 which moves close to and/or into contact with the lower layer 45 forms a conductive segment.

The lower layer 45 has a plurality of electrical contacts 51 which are each connected via a wire to the processing unit 27 in accordance with the embodiment of FIG. 2. In this embodiment, a pressure sensor 23 comprises a conductive wire portion 49, the electrical contact 51 arranged opposite and the recess 47 which accommodates them.

In the example described here, the electrical contacts 51 of the lower layer 45 are selected to have a contact surface 3 to 5 times greater than the contact surface of an electrical conductor 49 of the surface layer 41. This is because this facilitates the contact therewith during a deformation of the surface layer 41 following a pressure, and prevents detection errors. In different variants, however, the surface-area of the electrical contact 51 may be selected to be identical to that of the electrical conductor 49, or less.

In another embodiment, the sensors 23 may be push-buttons.

The covering component 1 is therefore provided so as to be installed with the lower layer 45 in contact with an existing floor and with the surface layer 41 as a contact surface for walking. To this end, the surface layer 41, advantageously at least the outer upper surface thereof, may be linoleum, plastics material, carpet or any other type of floor material or structure as defined by sanitary standards.

In a variant, the upper surface of the surface layer 41 may be provided in order to receive an additional layer of a conventional floor covering and optionally be provided with an adhesive which facilitates the fixing of the conventional covering. The covering components 1 are considered to be elements of a sub-layer of floor covering whilst the additional layer forms the surface layer, for walking. In this case, the flexibility of the surface layer 41, the sensitivity of the pressure sensors 23 and/or the conventional additional covering are adapted so as not to impair or neutralise the operation of the covering component 1. For example, the additional covering is selected to be sufficiently deformable so that, in the case of vertical pressure, the surface layer 41 is pressed into the recesses 47 at the location at which the pressure is applied, as described above. It is desirable to avoid additional coverings which are excessively rigid, such as tiling, which could distribute the application of forces acting on the component(s) and falsify the measurements.

Advantageously, the surface layer 41 may be selected to be more deformable than the intermediate layer 43 which may, for example, have a pressure resistance of approximately from 15 kg/m$^2$ to 25 kg/m$^2$. In this manner, the surface layer 41 may become deformed more readily inside the recesses 47 under the effect of pressure, which allows the detection sensitivity to be increased.

In the same manner, the lower layer 45 is suitable for acting as a connection to the ground. It may, for example, be of rubber which has non-skid properties, may be a material which is suitable for adhesion or comprise other fixing means.

Besides being superimposed, the layers 41, 43 and 45 are specifically arranged so that the conductor 49 is arranged opposite the recesses 47 or at least the vast majority thereof, so that the electrical contacts 51 are themselves opposite these recesses 47 or the vast majority thereof.

The body 3 of the covering component 1 comprises the lower layer 45 and the surface layer 41. These two layers 41, 45 are assembled at the mutual edges thereof in order to form the edges 5, 7, 9 and 11 described with reference to FIG. 1. The assembly in this instance is produced by means of welding in the region of the periphery. In a variant, the two layers 41, 45 are connected by means of weaving, bonding, crimping and/or any other suitable means. In another variant, the lower layer 45 and the surface layer 41 are formed by an integral component which is folded over on itself, one of the edges 5, 7, 9 and 11 then being formed by the fold whilst the other three edges are formed by the mutual assembly of the free edges. Generally, the body 3 forms a chamber or a casing which is protective and/or substantially sealed for the inner components of the covering component 1 relative to the external environment. In particular, the electronic components are protected from liquids which may be in contact with the component 1.

As illustrated in FIG. 8, when a pressure (illustrated in this Figure by an arrow), for example, the force applied by the weight of a person, is applied to the surface layer 41, it becomes deformed and fills the recesses 47 in the region of the location where this pressure is applied. The conductor 49 comes into contact with the electrical contacts 51 in the relevant recesses 47.

In the example described in this instance, the recesses 47 are spaced apart from each other in one or other of the main directions x and y of the covering component 1, centre to centre, at a distance of approximately 7.5 cm, and, if a covering component 1 is considered which has a surface-area of 1.6 m by 2.1 m, 252 pressure sensors 23 which are formed by the triplets conductor 49, recess 47, contact 51 are therefore obtained. Advantageously, the spacing between the recesses 47 may be between 5 cm and 20 cm.

Figure 13:
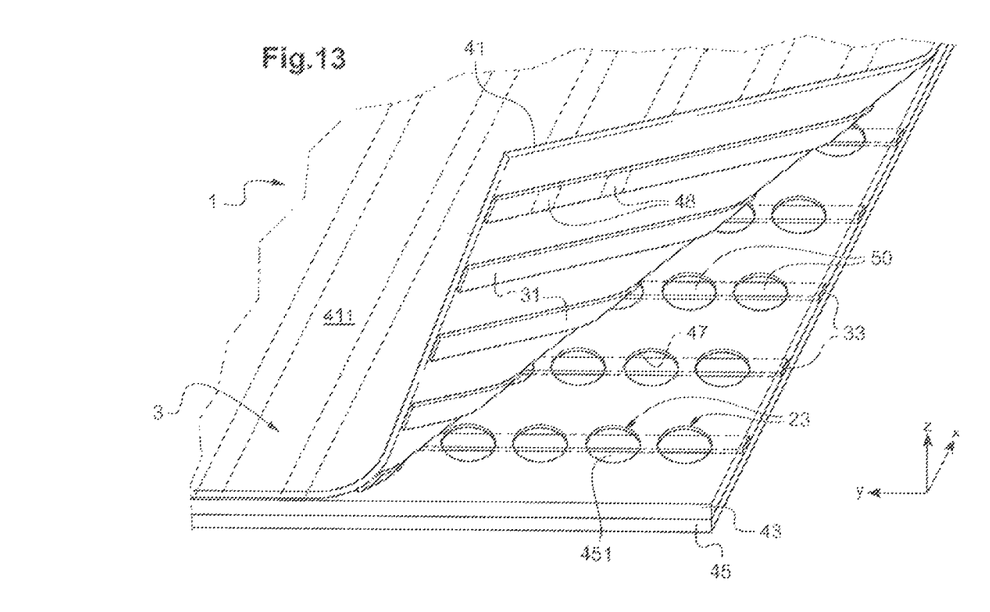
FIG. 13 is a broken-away view of an embodiment of a covering component according to the invention.

In the embodiment illustrated in FIG. 13, the elements which operate in a similar manner to those of the embodiments described above are numbered in an identical manner. The intermediate layer 43 has a thickness and a composition which are selected for their resilient or rigid properties. The surface layer 41 and the lower layer 45 are each produced based on a film 411 and 451, respectively, based on polyester, polyethylene or polyimide. The films 411 and 451 have thicknesses of between 1 and 5 mm, for example, 3 mm.

The faces of the films 411 and 451 which face each other, that is to say, which are orientated towards the inner side of the body 3, carry conductive strips 31, 33, respectively. The conductive plates 31 carried by the surface of the film 411 of the surface layer 41 directed towards the inner side form a set of conductive plates 31. The conductive strips 33 carried by the inner surface of the film 451 of the lower layer 45 directed towards the inner side form another set of conductive strips 33.

The conductive strips 31, 33 are produced in the form of tracks of copper, aluminium or any other suitable conductive material, by means of deposition or varnish, in order to form flat cables, that is to say, which have a small thickness relative to the surface thereof.

In a variant, the conductive strips 31, 33 of each of the sets are fixed to the film 411, 451, respectively, for example, by means of adhesive bonding or application of a heat-reactive resin. The conductive strips 31, 33 are then applied directly against the films 411, 451, respectively, by means of pressure between two rollers and under heat. This is then referred to as "coating": the material of the film is itself reactive to heat. It is possible to use as material, for example, a polyesterimide, which has good properties of adhesion to copper.

The conductive strips 31, 33 in this instance have thicknesses of between 30 and 200 μm, for example, 50 μm. The conductive strips 31, 33 have shapes which are substantially similar to each other. The length and width of the conductive strips 31, 33 are adapted to the dimensions of the component 1. In the example, the conductive strips 31, 33 have lengths which are slightly less than that of the component 1, that is to say, in this instance less than 50 cm. The conductive strips 31, 33 have widths of between 2 and 20 mm, for example, 6 mm.

The conductive strips 31, 33 are arranged in a flat state against the internal surfaces of the films 411, 451, respectively. The conductive strips 31 of the first set are parallel with each other. The conductive strips 33 of the second set are parallel with each other. The conductive strips 31, 33 extend in directions (x, y, respectively) in planes parallel with the main plane of the component 1. The conductive strips 31 of the first set extend in a direction (direction x) substantially perpendicular to that (the direction y) of the conductive strips 33 of the second set. The conductive strips 31, 33 are spaced apart from each other by a pitch which is substantially constant. The two sets of superimposed conductive strips 31, 33 form a substantially homogeneous and regular grid. The conductive strips 31 of the first set form a series of lines in the direction x. The conductive strips 33 of the second set form a series of columns in the direction y.

The conductive strips 31 of the first set cross the conductive strips 33 of the second set in the region of the recesses 47. The term "cross" is intended in this instance to refer to crossing seen in a direction perpendicular to the main plane of the component 1 (the direction z) without the conductive strips 31, 33 being in contact when the component 1 is not subjected to any stress. The conductive strips 31, 33 of each of the sets remain at a distance in the direction z of the thickness by the intermediate layer 43.

When a pressure which has a component in the direction z is applied in the region of crossing between the first set of strips and the second set of strips, the portion 48 of the conductive strip 31 and the portion 50 of the conductive strip 33 which correspond are brought into contact. An electrical contact is established between the relevant conductive strip 31 and the corresponding conductive strip 33, in the manner of a switch which closes. In this configuration, each crossing of the conductive strips 31 and 33 defines a pressure sensor 23.

Portions 48 of the conductive strips 31 are opposite portions 50 of the conductive strips 33 via recesses 47. Each pair of portions 48, 50 of conductive strips 31, 33 facing each other through a common recess 47 forms a pressure sensor 23. All of the pairs of portions 48; 51 of conductive stripes 31; 33 which are fixed to the inner surfaces of the films 411; 451 of the layers 41; 45 form a matrix of pressure sensors 23.

The processing unit 27 comprises a printed circuit, for example, an integrated circuit which is specific to an application (or ASIC, for "Application-Specific Integrated Circuit"), a programmable logic circuit (for example, known under the acronym FPGA or "Field-Programmable Gate Array") or an integrated system on chip (or SoC or "System on Chip").

In a preferred embodiment, the body 3 is generally rectangular or square. The processing unit 27 is arranged in a corner of the body 3. In this manner, the edges opposite this corner can be cut prior to the installation of the covering component 1. This allows the shape of the covering component 1 to be adapted when placed in position in accordance with the shapes and dimensions of the floor to be covered. The possibility of cutting must be understood in this instance to be a cut using scissors or conventional tools, such as a tiling knife which is generally available to an operator used to laying floor coverings. This is because, in the event of installation in a corner of a room, the two sockets provided on the opposing edges at the corner of the component in which the processing unit 27 is arranged are no longer useful. Therefore, the corresponding portion of the covering component 1 can be sectioned in order to accommodate the shape of the room in which the covering is placed. This therefore enables a large degree of flexibility of installation, and the covering component 1 can thus be produced in accordance with a standard pattern whilst being able to be adapted to complex or non-conventional shapes.

Embodiments of a covering component 1 have been described up to this point. However, and as set out above, the covering components of the invention are intended to be assembled with similar covering components in order to cover an existing floor. The covering component 1 is therefore arranged to be connected to other covering components which are similar or at least compatible. In this regard, it is advantageous to provide a group or batch of several covering components 1, for example, in the form of an installation kit.

Figure 9:
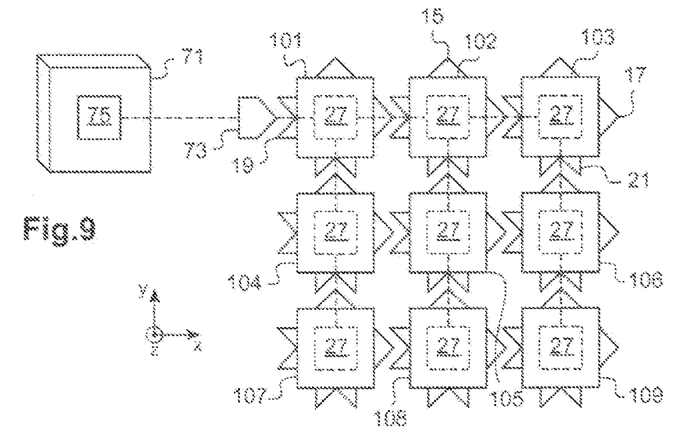
FIG. 9 is a schematic view of an assembly of a plurality of coating components according to the invention.

FIG. 9 shows an example of such an assembly comprising nine covering components 101 to 109 which are mutually organised in three lines and three columns.

The sockets 15, 17, 19 and 21 of the covering components 101 to 109 are arranged so as to be able to be connected to at least one of the sockets 15, 17, 19 and 21 of a juxtaposed covering component. In the example described in this instance, the north socket 15 and east socket 17 of each of the covering components 101 to 109 are of male form. In a complementary manner, the west socket 19 and south socket 21 of each of the covering components 101 to 109 are of female form. Generally, two sockets which are intended to be connected to each other have complementary shapes.

In an assembled state, as illustrated in FIG. 9, the floor covering components 101 to 109 are interconnected. The transmission of information between each processing unit 27 of each covering component 101 to 109 is made possible by the mutual connections of the sockets 15, 17, 19 and 21.

Such an arrangement of the sockets further enables a failsafe function. In this configuration, if the lower layer 45 of each covering component 101 to 109 is orientated towards the ground and the surface layer 41 is orientated in an upward direction, each covering component 101 to 109 is necessarily orientated in a similar manner to the others in order to be able to be connected thereto. Differences in textures, materials and/or colours between the visible surfaces of the surface layer 41 and the lower layer 45 enables reducing the risk of inversion of the two main faces of the components 101 to 109.

In a variant, the surface layer 41 and the lower layer 45 may be similar when the covering components are provided to be applied to the floor independently of the orientation of the surfaces. The covering components are reversible.

In a variant, the sockets may all be of the same type, for example, all male or all female. In this instance, there is provided a separate element, such as a jumper, to be interposed between two sockets to be connected, the jumper being, for example, of the female-female or male-male type. This variant has the advantages of requiring only a single type of socket and reduces the production costs. On the other hand, the orientation of the covering components may then be free, which facilitates the work of the operator during the installation of the covering. The components per se then have no restriction in terms of orientation during installation. The orientation of such a component is defined only a posteriori during the configuration and relative to the position thereof relative to other components, as will be described below.

In another variant, the sockets may be at least partially superimposed. That is to say, during the installation of a covering component in the immediate vicinity of a covering component which is already installed, a socket of the second component covers at least partially a socket of the first component. The connection is produced in a direction which is substantially perpendicular to the plane of the body. This allows the connection operation to be carried out substantially at the same time as the positioning with a substantially vertical movement. This variant can be combined with the variant having a jumper if each of the sockets is arranged so as to function both as a covered socket and as a covering socket.

In other variants, the sockets could be contactless devices for example, communicating elements of the capacitor or inductor type. In this instance, the sockets of two adjacent slabs may be arranged in the respective body of each slab and communicate with an associated socket through casings which are formed by the bodies of these sockets, without being accessible from the outer side. This facilitates the insulation of the inner side of the body relative to the external environment. The risk of infiltration of fluid via a socket in the covering component and damage is limited.

The assembly, in an operating state, comprises, in addition to the covering components 101 to 109, a central unit 71 or analyser for the detection of falls.

The central unit 71 comprises a socket 73. The socket 73 is arranged so as to be connected to at least one covering component 101 to 109, for example, via a socket 15, 17, 19 and 21 of the component. In this instance, the male socket 73 of the central unit 71 is connected to the west female socket 19 of the covering component 101 which is itself located in the north-west corner of the assembly.

The central unit 71 comprises a processor 75 which is connected to the socket 73.

After an assembly of covering components 101 to 109 has been installed on the ground and interconnected, the processor 75 is connected to a processing unit 27 of one of the covering components 101 to 109 and placed under voltage. Upon being switched on, or following a restart or a resetting to zero operation, the processor 75 carries out a configuration operation.

Figures 10, 11, 12:
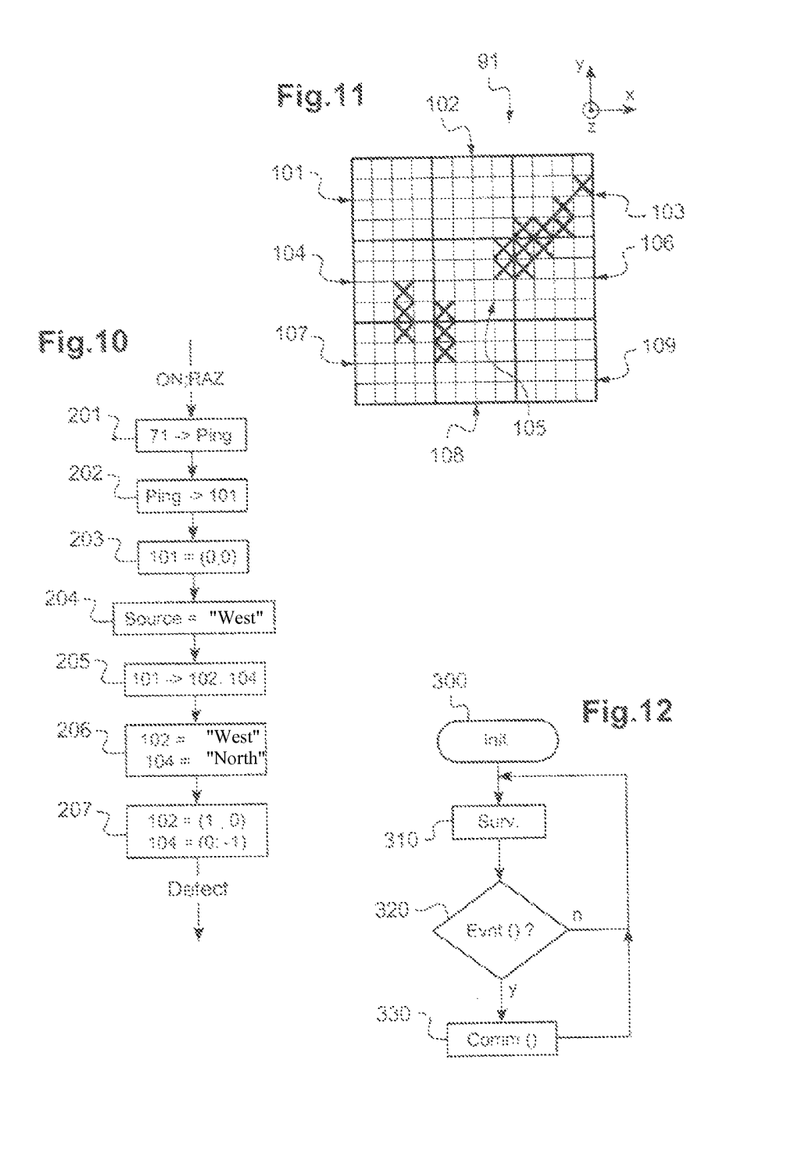
FIG. 10 is an example of a flow chart of a configuration function of the assembly of FIG. 9.
FIG. 11 is a view in the form of a state matrix of an assembly of pressure sensors.
FIG. 12 is an example of a flow chart of a function implemented in the invention.

FIG. 10 is a flow chart which the processor 75 and the processing units 27 can implement to this end. In an operation 201, the processor 75 transmits a configuration signal or "ping" via an output of the central unit 71, and in this instance the socket 73.

In an operation 202, the configuration signal is received by a first covering component to which the socket 73 is connected, that is, the component 101 in the case of the arrangement of FIG. 9. The signal is received by the processing unit 27 of the component 101 via one of the sockets, in this instance the west socket 19. The processing unit 27 identifies the configuration signal and the source socket, in this instance the west socket 19, via which the signal has been received.

The configuration signal comprises the location identifier of a first single component to which the central unit 71 is connected, in this instance the covering component 101. This identifier is in this instance a pair of coordinates in a plane which corresponds to the floor of the type (x; y) and which fixes an origin (0; 0). As will be described below, the fixing of this origin allows the propagation of the information to be defined within the assembly of components 101 to 109 and the central unit 71. This location identifier in this instance becomes both a piece of identification information of the component 101 and a piece of location information of the component 101 relative to the assembly.

In an operation 203, the processing unit 27 of the component 101 interprets the configuration signal as a designation of the covering component 101 as the first component of the assembly. The processing unit 27 stores in the memory thereof the location identifier (0; 0) of the covering component 101.

In an operation 204, which can be carried out before, during or after the operation 203, the processing unit 27 interprets the source of the configuration signal as a designation of the source socket, in this instance the west source 19. For example, the processing unit 27 stores in the memory thereof an identifier of the source socket or input. This identifier is in this instance "west". The fixing of this orientation also allows the propagation of information within the assembly of components 101 to 109 and the central unit 71 to be defined. The west socket 19 is defined as an input.

In a variant, the configuration signal transmitted by the central unit 71 is blank, that is to say, it does not comprise any location identifier. In this instance, each processing unit 27 is arranged so as to allocate a location identifier which fixes the origin (0; 0) to the covering component to which it belongs in response to the reception of the blank configuration signal.

In an operation 205, the processing unit 27 of the first component, in this instance 101, transmits modified configuration signals. Each of these modified configuration signals is sent to one of the other three sockets 15, 17, 21 which then become outputs. The modified configuration signal comprises, in this instance, the location identifier of the transmitting covering component 101, the location identifier of the receiving covering component 102, 104, respectively, and the identifier of the source socket, in this instance "west" for the component 102 and "north" for the component 104. The processing unit 27 of the component 101 determines the identifier of the component 102, 104, respectively, in accordance with the identifier of the transmitting covering component 101 and the socket via which the signal is transmitted. For example, the identifier to be transmitted via the east socket 17 of the component 101 corresponds to that of the component 101 whose coordinate relative to the direction east-west (x) is increased by 1, that is, (1; 0). In a similar manner, the identifier to be transmitted via the south socket 21 of the component 101 corresponds to that of the component 101 whose coordinate relative to the direction north-south (y) is decreased by 1, that is, (0; −1). The identification information to be transmitted is selected in this instance in an iterative manner by the processing units 27.

In an operation 206, each modified configuration signal is received by each of the covering components 102, 104, which are called receivers and which are connected to one of the three output sockets 15, 17, 21 of the transmitting component 101. The signal is received by the processing unit 27 of each of the components 102, 104 via one of the sockets, in this instance the west socket 19 of the component 102 and the north socket 15 of the component 104. Each of the processing units 27 identifies the modified configuration signal and the socket via which the signal has been received. The processing unit 27 stores in the memory an identifier of the source socket, in this instance the west socket 19 for the component 102, or the north socket 15 for the component 104, respectively. This socket is then defined as the input socket.

In an operation 207, each of the processing units 27 interprets the modified configuration signal. In this instance, each processing unit 27 stores in the memory the location identifier (1; 0), (0: −1), respectively, of the covering component 102, 104, respectively, to which it belongs and the location identifier (0; 0) of the source covering component 101 included in the signal received from the transmission component 101. The processing unit 27 calculates the location information of the component in accordance with other location information. This calculation is iterative.

Then, each of the receiving components 102, 104 transmits in turn the signal via each of the other three sockets which are not defined as being inputs and are therefore defined as outputs. This operation is similar to that of the operation 205, the receiving components 102, 104 in turn becoming transmitters of the modified configuration signal for the other juxtaposed components 103, 105, 107. For example, the processing unit 27 of the covering component 102 determines by means of comparison of the location identifiers of the components 101 and 102 that the components 101 and 102 are aligned in the direction corresponding to the coordinate x. This is because the coordinate x has been increased between the covering components 101 and 102. This allows the processing unit 27 of the covering component 102 to calculate the manner in which to increase (or decrease) its own location identifier (1; 0) in order to calculate the location identifiers to transmit to each of the output sockets, in this instance: (2; 0) via the east socket 17 intended for the covering component 103 and (1; −1) via the south socket 21 intended for the covering component 105. The configuration signal is thus transmitted gradually in order to successively configure each of the connected components of the assembly.

The processing units 27 are configured to ignore the configuration signals after the location identifier and the "input" socket are fixed and stored in the memory of the processing unit 27 so as to define only a single and unique "input" socket. For example, in the case of the component 105, the processing unit 27 of this component will process only the signal received from the component 102 or only the signal received from the component 104. This feature is reversible and can be cancelled by a reset command. For example, a specific signal transmitted by the central unit 71 can erase information stored in the memory of the processing units 27.

In a variant, the transmission of the configuration signal can be limited to some output sockets only in order to limit the exchange of information.

In a variant of the configuration process, the activation status of the pressure sensors 23 of each of the covering components 101 to 109 is detected then fixed as a reference status. If, during this calibration step, some pressure sensors 23 are detected as being activated (a pressure is detected), then the processor 75 ignores the status information relating to these sensors 23 in the future and during operation. This calibration is carried out when no one is located in the room but the usual furniture is present. In this manner, pressure sensors 23 which detect a pressure, resulting, for example, from the weight of an item of furniture, can be neutralised or at least ignored during the calculations described below. In this manner, the presence of furniture preserves the operation of the measurement and therefore the truthfulness of the alerts.

In another embodiment, the calibration can be generated at a regular interval by sending a configuration signal via the processor 75, for example, every six hours. In this embodiment, the lack of a connection between two sockets of two juxtaposed components can be resolved automatically. The configuration signal could be transmitted gradually by taking a path which avoids the defective connection. The appropriate path or diagram of transit of information or routing is thus defined as long as the active connections are adequate. This embodiment is adapted for covering components which comprise more sockets than strictly required, for example, four. In this embodiment, the neutralisation of some sensors 23 may be provided when a pressure is detected in a systematic manner during successive calibrations.

After a component has been configured, that is to say, the location identifiers thereof and the identifier of the source socket have been recorded in the memory of the processing unit 27 thereof, this component switches from the configuration state to a detection state.

In the detection state, each processing unit 27 transmits a status message. This status message comprises the "pressure detected" status or "no pressure detected" status of at least some of the pressure sensors 23 which are connected to the processing unit 27. This transmission is carried out via the input socket whose identifier is stored in the memory of the processing unit 27. In a detection state, the "input" sockets of the configuration phase are used as outputs and vice versa. The status message further comprises a location identifier of each of the sensors 23 relative to the component in question, the location identifier of the component established during the configuration process and a time marker. The pairing location identifier of the component/location identifier of the sensor in the component enables each of the sensors 23 of the assembly to be identified and located. Each processing unit 27 associates this information in order to form the message. That is to say, in addition to the activation status and the identification of each of the pressure sensors 23 which are connected thereto, the processing unit 27 applies a marker containing location information of the component in order to distinguish the information from two similar sensors of two separate components. This will, a posteriori, enable recognition of the covering component which carries the pressure sensors 23.

In the example described in this instance, the status of each of the sensors 23 or only those whose status has changed is included in a message which is transmitted at predefined time intervals.

In a variant, as soon as a change of status of a sensor 23 is detected, the status of all of the sensors 23 is included in the message.

In another variant, the message is transmitted only when a change of status of at least one of the sensors 23 is detected and only the status of the sensors 23 for which a change has been detected are included in the message. This is then known as "active waiting" or "polling".

On the other hand, in a detection state, each processing unit 27 which receives a status message via one of the "output" sockets transmits this message via the "input" socket thereof. In this manner, the status messages are transmitted gradually in the reverse direction to that taken by the signal during the configuration operation in order to travel as far as the processor 75. The processing unit 27 transmits the associated information and the information received at predefined time intervals. Such an arrangement of the processing unit 27 enables the information from different origins to be gathered in order to be transmitted via a limited number of channels, in this instance the input socket.

The processor 75 collects all of the status messages of each of the components 101 to 109 of the assembly.

The processor 75 calculates, from the information taken from the status messages of the covering components 101 to 109, a mapping or status matrix 91 of the pressure sensors 23 of the interconnected covering components 101 to 109. A mapping 91 of the status of each of the pressure sensors 23 of each of the covering components 101 to 109 of FIG. 9 is illustrated schematically in FIG. 11.

The spaces marked by a cross illustrate an active pressure sensor 23, that is to say, which detects a pressure greater than a selected detection threshold. The empty spaces illustrate inactive pressure sensors 23, that is to say, which detect a pressure lower than the predefined detection threshold.

The calculations required for the detection can be carried out within the central unit 71. To this end, it may comprise a calculation unit in the form of an on-board device, a dedicated map or any other appropriate means. The central unit 7 may also comprise communication means, wired (via conventional telephone line or via a network, for example, Ethernet) or wireless (via a communication interface or module GSM, GPRS, 3G or WiFi). The communication module is connected to the output of the processor 75.

Furthermore, the central unit 71 may be produced in several portions. In this instance, the central unit 71 comprises a first portion which includes the processor 75, which is connected to the pressure sensors 23 and which comprises a communication interface similar to that described above.

The first portion communicates with a second remote portion which may carry out the detection calculations mentioned below, and may itself comprise a communication interface which is similar to that described above.

These communication interfaces or modules may be used in order to transmit alerts in the event of a fall being detected, for example, to a central server, to a central telesurveillance station, to an assistance call centre, to the nursing station in the case of a hospital, a clinic or a retirement home, etcetera.

Finally, the central unit 71 may include only a communication interface which is similar to the one described above, all of the calculations for the detection of a fall being remote on a detection server to which the central unit 71 is connected via this interface.

FIG. 12 shows an example of a flow chart that the fall detection calculation unit can carry out.

In an operation 300, the calculation unit is initialised, with all the parameters connected with the detection of falls, and with the initialisation of the communication interface.

Then, in an operation 310, a detection loop begins. This loop comprises the collection of status of the pressure sensors 23 of the components 101 to 109, that is to say, the data which correspond to the status matrix 91.

Then, in an operation 320, the calculation unit verifies the list of identifiers of pressure sensors 23, location identifiers of the components and time markers in order to determine whether these verify one of the conditions for the detection of a fall described below.

If this is the case, the communication interface is then activated in an operation 330 in order to send a fall detection signal, then the detection continues with the operation 310. If not, the loop continues directly with the operation 310.

The sending of the fall detection signal may comprise all the useful information, including the location of the fall derived from the identification of the pressure sensors 23 involved and the component(s) 101 to 109 which comprise them, a time period associated with the time markers in order to indicate the time of the fall, etcetera.

When a person falls, he is necessarily in an extended position on his back, on his stomach, or at least with a quite extensive portion of his body on the ground. A sufficiently tight mesh thus allows the difference to be detected between a fall and the presence of one or more persons standing on all the covering components 101 to 109.

The mesh of the example described with reference to FIGS. 7 and 8 is tight, which provides a high level of precision. The extent of a person lying down signifies that it is possible to detect a fall:

when more than ten detection locations, that is to say, pressure sensors 23, are activated in a square having a side of approximately 30 cm, or in a rectangle which has a similar surface-area and whose diagonal line is approximately 35 cm long, that is, over a surface-area of approximately 0.09 m$^2$, for a minimum length of time, for example, in the order of one minute, or when four detection locations which are aligned in a first main direction, diagonally or in a second main direction are activated for a minimum period of time, for example, in the order of one minute.

Generally, the minimum period of time for the detection may be selected to be greater than 15 seconds. In a variant, the detection may not be dependent on a minimum period of time.

In accordance with the arrangement of the sensors in the components and in particular their mutual spacing, the calculation algorithm is adapted, for example, to be able to select the precision of the measurement.

This is because these scenarios exclude the case of walking or the presence of several people on the floor which is covered with the components 101 to 109. An adult foot in the vast majority of cases has a length of less than 35 cm, which corresponds to a shoe size 53. Consequently, the detection criteria described above allow the upright position to be discriminated, in which only the feet are in contact with the ground. Furthermore, when several people are present, even if they are very close together, they will not bring about any detection owing to the meshes described, even if the centre-to-centre distance of the recesses 47 is 20 cm.

In a variant, the calculation unit may be parameterised in order to activate a specific alert signal in the case of detection of an individual who is standing or walking. The invention allows, in addition to the detection of falls, the detection of an intrusion or generally the presence and the location of a person, whether or not he is standing upright. The analysis of such data a posteriori is made precise and efficient when it is coupled to a data storage system. In the context of health establishments which receive elderly persons, such a parameterisation allows, for example, the rapid detection and location of a person lost in the establishment. This type of function is particularly advantageous for persons affected by memory problems.

In another variant, the activation and/or deactivation of some functions, for example, those described in the paragraph above, may be automated. For example, the activation of an alert in the case of a person standing upright may be activated only during predetermined time ranges, such as the night.

Such covering components, whilst being configured and produced using industrial processes, allow the provision of good adaptability at the time of installation in the spaces to be equipped. Bedrooms or corridors of retirement homes may be equipped using the covering components described above and by adapting the number and mutual arrangement thereof, as is known to be done for tiling, for example. In this instance, the interconnection of the covering components enables a network of sensors to be created in accordance with a very large number of combinations. The number of covering components required is substantially proportional to the total surface to be covered. On the other hand, the mutual assembly of the covering components is facilitated, which reduces the risk of errors and defects in positioning.

In the examples described above, the solutions proposed were selected with preference being given to the homogeneity of the covering components used in order to facilitate the work of operators carrying out the installation of these coverings and to limit the risk of errors during installation. For example, it is easy to install and combine an assembly of substantially rectangular components, each of the sides of which is provided with a socket.

Depending on circumstances, it may be preferable to minimise the costs of producing components and/or refining the compliance of the covering components with the surfaces to be covered. To this end, specific components may be adapted for a specific use. For example, there may be arranged rectangular covering components which have no socket on one or two of the sides for installation along a wall or in a corner. For the same reasons, the covering components may all be provided with only two sockets in order to define a single inlet and a single outlet and therefore a single gradual routing of information. In this case, the mutual arrangement of the sockets of a component and the mutual arrangement of the components of an assembly are dependent and require adaptation on a case by case basis.

The invention is not limited to the examples of covering components described above, only by way of example, but it includes all the variants which could be envisaged by a person skilled in the art in the context of the appended claims.

The invention also relates to assembly kits which comprise a plurality of covering components or tiles as described above. Such an installation kit may further comprise a central unit as described above.

The invention also relates to the fall detection method comprising:

acquiring the status of a set of pressure sensors which are arranged in a plurality of covering components which are connected to each other, transmitting status data from the sensors derived from the acquisition of the plurality of covering components to a central unit, detecting for a nominal selected period of time at least one of these conditions:

contiguous pressure sensors in the state "subjected to pressure" correspond to a surface-area which is greater than a predefined threshold value, or location data which are associated with pressure sensors in the state "subjected to pressure" indicate a continuous alignment of sensors, the two end sensors of which are remote by a distance greater than a predefined threshold, transmitting an alert signal in response to the detection of one of these two conditions.

The invention claimed is:
1. A fall detection flooring system, comprising:
at least a first and a second floor component, each component comprising:
a body comprising edges;
a plurality of pressure sensors distributed in accordance with the geometry of the body;
a component processing unit connected to at least some of the pressure sensors and arranged to collect status information of the connected pressure sensors; and
a first socket and a second socket each of which is connected to the processing unit and each arranged in a separate region of an edge of the body and at least one of the first and second socket of one of the first and second floor component connectable to at least one of the first and second socket of an opposite of the first and second floor component;
a central floor detection unit comprising:
a central unit socket connected to at least one of the first and second examiner's amendment examiner's amendment d socket of the first floor component; and
a central processor connected to the central unit socket and communicating with the component processing unit of both the first and second floor components;
wherein at least one of the edges is configured to be altered and the floor component remains operational with at least one of the plurality of sensors, at least one of the first and second sockets and the component processing unit;
wherein the component processing unit:
associates location information derived from the status information with location information of the respective component;
receives, via the at least one of the first and second socket, information originating from the other of the first and second floor component; and
transmits, via an opposite of the first and second socket, at least one of the associated information and the received information to the other of the first and second floor component;
wherein the central processor:
assigns unique floor component location identification information to the first and second floor components;
collects status information and location information of the pressure sensors from the component processing unit of at least one of the first and second floor components;
calculates, using the unique floor component location identification information, the pressure sensors status information, and the location information, a status matrix of the first and second floor components;
detects and alert status from the status matrix indicating a fall; and
transmits an alert signal which is selected in accordance with the alert status detected.

2. The fall detection flooring system according to claim 1, wherein the component processing unit is arranged to transmit the associated information and the received information at predefined time intervals.

3. The fall detection flooring system according to claim 1, wherein the component processing unit is arranged so as to transmit associated information in response to status modifications of the pressure sensors.

4. The fall detection flooring system according to claim 1, wherein the body further comprises:
a surface layer
a lower layer; and
an intermediate layer being arranged between the surface layer and the lower layer and comprising a plurality of recesses which at least partially accommodate the pressure sensors.

5. The fall detection flooring system according to claim 4, wherein the surface layer and the lower layer each comprising a film which carries, on opposing faces, a set of conductive strips, the conductive strips being substantially parallel within each set, and the sets of conductive strips being arranged so that the conductive strips of separate sets are substantially perpendicular to each other and cross each other in the region of the recesses of the intermediate layer, in order to form a pressure sensor each time.

6. The fall detection flooring system according to claim 1, wherein the body is generally rectangular or square, the component processing unit being arranged in a corner of the body.

7. The fall detection flooring system according to claim 1, wherein the component processing unit is further arranged to calculate first and second floor component location information in accordance with other location information.

8. The fall detection flooring system according to claim 7, wherein a first component processing unit is arranged in order to calculate the identification information of the second floor component in accordance with identification information of the second floor component in an iterative manner.

9. The fall detection flooring system according to claim 1, wherein the body has a flattened shape whose surface-area is between 400 cm$^2$ and 2.25 m$^2$.

10. The fall detection flooring system according to claim 1, wherein the first socket and the second socket are mutually arranged so as to form a failsafe for the installation of the first and the second floor components.

11. The fall detection flooring system according to claim 1, further comprising a communication module which is connected to the output of the central processor and which is arranged so as to transmit the alert signal to a central server.

12. The fall detection flooring system according to claim 1, wherein the central processor is arranged so as to ignore the status information of at least some of the pressure sensors.

* * * * *